US006998214B2

(12) United States Patent
Fourkas et al.

(10) Patent No.: US 6,998,214 B2
(45) Date of Patent: Feb. 14, 2006

(54) METHODS FOR THREE-DIMENSIONAL OPTICAL DATA STORAGE AND RETRIEVAL

(75) Inventors: John T. Fourkas, Chestnut Hill, MA (US); Christopher E. Olson, Boylston, MA (US); Michael J. R. Previte, Peabody, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 133 days.

(21) Appl. No.: 10/194,106

(22) Filed: Jul. 12, 2002

(65) Prior Publication Data

US 2003/0027063 A1    Feb. 6, 2003

Related U.S. Application Data

(60) Provisional application No. 60/305,053, filed on Jul. 13, 2001.

(51) Int. Cl.
*G11B 7/26* (2006.01)
(52) U.S. Cl. ............. 430/269; 430/270.15; 430/945; 365/106
(58) Field of Classification Search ........... 430/269, 430/270.15, 945; 315/106
See application file for complete search history.

(56) References Cited

U.S. PATENT DOCUMENTS

| | | | |
|---|---|---|---|
| 3,931,228 A | 1/1976 | Borror ............... 260/326.12 R |
| 4,466,080 A | 8/1984 | Swainson et al. ........... 365/106 |
| 4,471,470 A | 9/1984 | Swainson et al. ........... 365/127 |
| 4,499,165 A | 2/1985 | Molaire .................. 430/9 |
| 4,613,878 A | 9/1986 | Inaba et al. ................ 346/204 |
| 4,938,224 A * | 7/1990 | Rysavy .................... 600/317 |
| 5,034,613 A | 7/1991 | Denk et al. .............. 250/458.1 |
| 5,289,407 A | 2/1994 | Strickler et al. ............ 365/106 |
| 5,325,324 A * | 6/1994 | Rentzepis et al. .......... 365/127 |
| 2002/0015858 A1* | 2/2002 | Kaneko et al. ............. 428/689 |

FOREIGN PATENT DOCUMENTS

| | | | |
|---|---|---|---|
| JP | 04-036381 | * | 2/1992 |
| JP | 06-100552 | | 4/1994 |
| JP | 06-266110 | | 9/1994 |
| WO | 99/23650 | * | 5/1999 |

OTHER PUBLICATIONS

Merck Index, tenth Ed. p. 369,370,1043,1044 and 1348 (1983).*
Heuberger, et al.; "Size Dependence of Tracer Diffusion in Supercooled Liquids"; (1996); *J. Phys. Chem.*; 100: 15255-15260.
Chang, et al.; "Heterogeneity at the Glass Transition: Translational and Rotational Self-Diffusion"; (1997); *J. Phys. Chem. B.*; 101: 8794-8801.

(Continued)

*Primary Examiner*—Martin Angebranndt
(74) *Attorney, Agent, or Firm*—David J. Dykeman; Palmer & Dodge

(57) ABSTRACT

A three dimensional optical data storage and retrieval system that includes a three dimensional optical data storage medium and an apparatus for providing access to data stored on the medium. The data storage medium includes an optical data storage material which either a low molecular weight or polymeric glassy solid that are capable of undergoing multiphoton excitation that are energetically different in the write and read cycles. The optical data storage materials provide substantially higher storage capacities relative to conventional materials, and show high robustness in that written and stored data can undergo multiple read cycles without erasure or overwriting. An apparatus for data recording and accessing stored data on the medium includes a controllable variable energy photo-emitting excitation source and an emission photo-detector.

22 Claims, 6 Drawing Sheets

OTHER PUBLICATIONS

Koyanagi, et al.; "A New Positive-acting Chemically Amplified Resist System for Electron-beam Lithography"; (1992); *Proc. SPIE*; 1672: 125-140.

Copy of International Search Report for International Application No. PCT/US02/22264 dated Dec. 10, 2002.
Supplementary European Search Report EP 0275 0015.

* cited by examiner

1μm

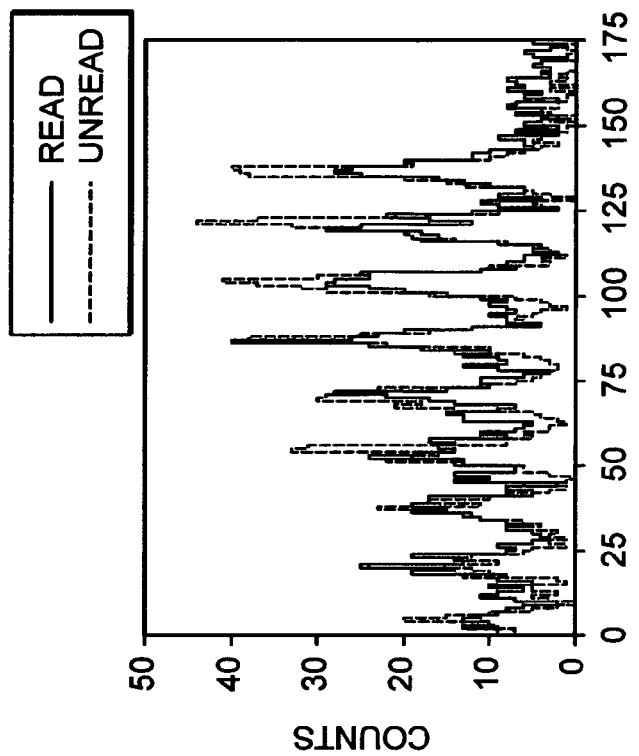
FIG. 3B
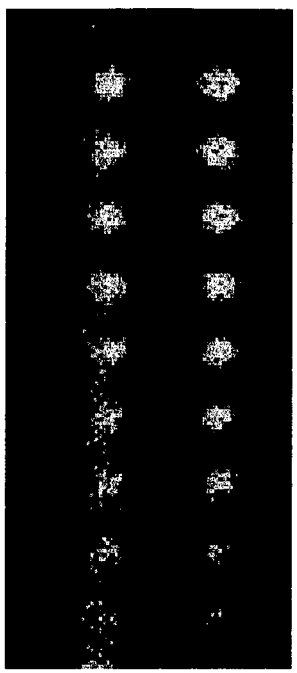
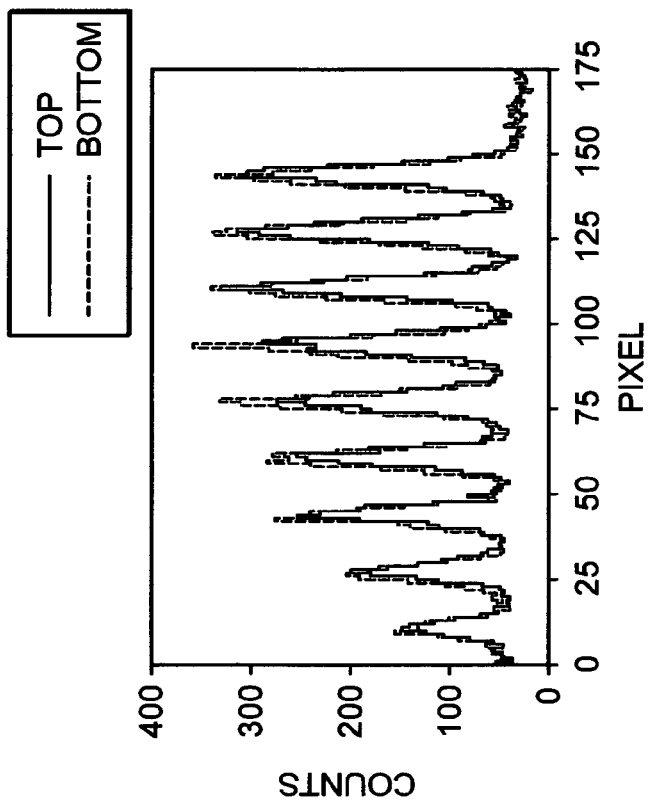
FIG. 3A
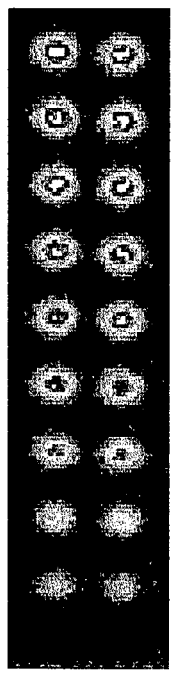

METHODS FOR THREE-DIMENSIONAL OPTICAL DATA STORAGE AND RETRIEVAL

This application claims priority to U.S. Provisional Application Ser. No. 60/305,053 filed on Jul. 13, 2001.

STATEMENT AS TO FEDERALLY FUNDED RESEARCH

The present invention was made with support in part from the Air Force Office of Scientific Research Grant No. F49620-01-1-0455. The United States Government retains certain rights to the invention.

FIELD OF THE INVENTION

The present invention relates generally to the synthesis of optical data storage materials that form stable solids capable of undergoing a multi-photon excitation, and apparatus and methods for their use in optical data storage media, particularly for three-dimensional optical data storage and retrieval.

BACKGROUND OF THE INVENTION

Conventional two-dimensional (2-D) optical data storage is accomplished by using photonic excitation of the storage material in the visible or infrared wavelengths at the diffraction limit. The theoretical limit for storage density in a 2-D system is typically ~$10^8$ bits/cm$^2$. With the presently growing need for economically viable, high performance computers with increased memory and storage capacity, optical storage media that provide the capability writing and reading data in a three-dimensional (3-D) format (with a theoretical storage capacity of >$10^{12}$ bits/cm$^3$) offers a potential solution for enabling compact, low-cost, high-speed memory devices with high storage capacities. Optical storage of information inside the volume of a 3-D storage or "memory" device is usually accomplished by inducing chemical changes via photonic processes (typically in the ultraviolet range) in micro-domain areas in a 3-D mode within an optical storage material comprising an optical storage media. "Optical storage materials" as used herein refers to materials (including chemical compounds) that are capable of undergoing a photo-induced change that can be subsequently monitored. "Optical storage media" as used herein refer to suitable forms and configurations of the optical storage materials so as to render them capable of presenting themselves in a 3-D matrix to an optical source in a manner that enables irradiation of micro-domains within the matrix in a pre-determined pattern representing an information set. The information (or data) storage process is termed "writing", which denotes irradiation of the photon-absorbing "write" form of the molecules within the storage medium, transforming them into either a visible-light-absorbing form, or cause a change in their light transmission properties. Molecules that have undergone these changes are denoted to be in the "written" form. The stored data is accessed (or retrieved) by "reading", which refers to probing the "written" form of the molecules with a photon source and by monitoring their optical response such as emitted fluorescence or changes in transmission due to altered refractive index.

Presently, two approaches are adopted for providing 3-D optical storage memory in materials. The first involves optically writing in micro-domains within the optical storage material whereby a change in the local refractive index of the material is introduced in the written micro-domains. The differential refractive index pattern is then subsequently read using standard optical methods. The second approach is to use optical storage materials that either include photochromic molecules, or polymers that are capable of undergoing photobleaching that may be additionally doped with chromophores such as dye molecules. Optical changes are photonically introduced in the dye molecules causing them to emit radiation in the visible range that are subsequently monitored. Although such materials are theoretically capable of providing bit densities of terabits per cubic centimeter, they have not been proven to be commercially viable for providing stable 3-D storage media.

Conventional 3-D optical storage media may be categorized into two types. The first constitutes a recordable medium comprising a stack of 2-D bit arrays that multiply the data density by the number of planes in the resulting 3-D stack. This type of optical data storage and retrieval processes in storage media has been conventionally accomplished by utilizing a multi-photon excitation process. It involves a two-photon excitation step to initiate the "write" process, whereby a photochemical reaction is induced in micro-domains within the medium that induces a permanent chemical change in the said domains. For optical storage media that are comprised of a polymeric matrix impregnated with a photoactivatable dye, the chemical change involves transformation of the dye, for example, into a fluorescent moiety. The written micro-domains comprising stored data can be subsequently "read" by photo-irradiation that causes them to emit fluorescence. U.S. Pat. Nos. 4,466,080 and 4,471,470 disclose the use of a plurality of intersecting beams to localize the writing and reading of information in 3-D photochromic optical memory media. U.S. Pat. No. 5,034,613 discloses a more simplified method that utilizes a single highly focussed beam to record and read information via a two-photon excitation. A two-photon photoactivation of a fluorescent dye that is non-fluorescent until photochemically modified has been also reported. However, the useful lifetime of such two-photon excitation processes that rely on fluorescence modulation is limited by photobleaching that occurs with multiple reads of the written data. This limitation may be attributed to the fact that the photoexcitation energies for the read process in these media induce photochemical degradation or crosslinking of the polymeric matrix and render them optically less transmissive. Thus the data stored within the media can no longer be read efficiently by the optical source. Another major limitation in this type of media is "cross-talk" between the planes, wherein the excitation beam strongly contaminates the planes above and below the focal plane on which data is being written. Since writing with 3-D resolution in these stacked array systems is accomplished by a nonlinear two-photon excitation of the medium to confine data storage to the focal plane, such contamination or "cross-talk" seriously limits both storage capacity and integrity of stored data.

The second approach for providing 3-D optical storage media uses storage materials that are capable of undergoing a photochemically induced localized change in material refractive index during the "write" process. This is accomplished by initiating a photochemical reaction such as photo-crosslinking in micro-domains within the material, thereby causing a localized change in the material refractive index of said domains relative to the surrounding media. These changes are subsequently "read" by an optical source that is capable of recognizing the change in light transmission properties within the material caused by the alteration in refractive index. U.S. Pat. No. 5,289,407 discloses a technique for writing and reading data in a three dimensional multi-layered format wherein information is written as submicron voxels (i.e. domains that are processible by means of visualizing 3-D shapes and structures by utilizing a series of cross-sectional images) of modified refractive index domains that are induced by a photo-crosslinking reaction initiated by a two-photon excitation process of a polymeric medium. An array of optically refractive "beads" is formed in a plurality of stacked planes. The written information is subsequently read with 3-D resolution using differential interference contrast microscopy. Although such storage media are not susceptible to photobleaching as in the case of the fluorescent dye impregnated type, their limitations include the following: 1) The photopolymer comprising the medium has to be irradiated with UV light prior to its use for writing optical data to gel the sample in order to prevent distortion due to shrinkage and flow, and 2) This pre-gelation process typically results in crosslink densities within the polymeric medium that are non-uniform, thereby resulting in varied refractive indices within the bulk medium. This, in turn, can result in reduced storage capacity due to domains of high crosslink density or "dead-spots" within the gel that are non-writable, as well as substantial loss in sensitivity for reading stored data.

Another drawback in existing optical data storage and retrieval methods in conventional media is that the photon excitation energies for the write and the read process are substantially similar. In dye-doped polymer media, for example, the data writing process typically involves a two-photon excitation of the impregnated dye matrix in micro-domains so as to render the dye in the said domains to become it fluorescent. The written micro-domains are subsequently read by photoexcitation of the fluorescent domains and analyzing their emission patterns. Since the "read" process requires photon energies that are similar in magnitude as those required for writing, written data can be contaminated by "overwriting" during the read process. This limitation is inherent in optical storage media that function via a photo-induced optical refractive index change during the write process, since the subsequent optical read process can cause contamination or "overwrite" problems, resulting in data degradation ("memory loss") over multiple read cycles.

SUMMARY OF THE INVENTION

The present invention provides optical data storage materials for producing high memory capacity storage media, and apparatus and methods for writing and reading data in said storage media in a three-dimensional, multi-layered format. More particularly, the present invention provides a class of materials comprising bisphenol and phthalein diether compounds and their derivatives, and cross-linked epoxy polymers for optical data storage. The optical data storage materials of the present invention become highly fluorescent upon exposure to a multi-photon activation (MPA) of 800-nm pulses of light from a Ti:sapphire oscillator, thereby rendering them excellent for 3-D optical data storage. The optical data storage materials of the invention are relatively inexpensive, obtainable in high optical quality, can be processed readily, and can be obtained as low molecular-weight glasses, as well as cross-linked glassy polymers. 3-D data storage can be accomplished optically at high densities in the materials storage media of the invention that are highly stable and substantially free of "memory loss" due to material degradation over multiple read cycles.

The optical storage media of the invention comprise glassy materials obtained from compounds, that when heated above their melting points and subsequently cooled to room temperature, form optically clear glasses (herein referred to as "molecular glasses"). In their glassy state, these compounds are converted to fluorescing moieties when subjected to a MPA process activated by exposure to multi-photon excitation from a laser source, which in turn, produce highly fluorescent emissions. Data storage in optical media comprising materials is accomplished by the writing method of the invention which uses a multi-photon fluorescence microscope in conjunction with a mode-locked Ti:Sapphire laser that is centered around 800 nanometers (nm) and is capable of providing a tightly focused excitation beam. The MPA process causes a chemical transformation of molecules located in the irradiated micro-domains within the molecular glass to become fluorescent. The written or stored information can be subsequently retrieved by optically reading the created photoactivation pattern. Since fluorescing molecules are generated only where the excitation beam is incident and only proximal to the focal point of the laser beam, three-dimensional writing and reading of information is rendered viable by focusing the beam at varying depths within the optical media. The power, duration and focal size of the writing beam incident on the media can be varied to produce written bits of different volumes. Storage densities of up to 1 gigabyte per square centimeter are possible using the materials and methods of the invention. Reading of stored information can be accomplished by the method of the invention wherein a photoexcitation "reading" beam causes molecules in the written domains to undergo a multi-photon absorption, and the resulting fluorescence emitted from said domains is optically detected by the detection apparatus of the invention. The reading beam can be optimized to maximize the signal-to-noise ratio (S/N) of the written bits, thereby increasing sensitivity, while substantially minimizing memory degradation from multiple reading cycles. On the other hand, stored data can be "erased" by performing an overwrite using the higher energy, three-photon excitation process, for example, to remove data that is no longer needed.

Another aspect of the optical media of the invention that is a key feature to their durability, that is, ability to withstand multiple read cycles (up to 2,000,000 reads) of written material without suffering memory degradation due to overwriting or photobleaching is that the multiphoton processes for the write and read modes are substantially different in terms of energy requirements. The write process is a three-photon process and requires energies that are substantially greater than the read cycle, which is a two-photon process with a lower energy requirement. The reading process therefore does not cause inadvertent overwriting that can result in memory degradation.

Information is written in the media as a result of a multi-photon excitation (MPE) step within the volume comprising the by a highly focused mode-locked laser, that causes a (MPA) process within the media at the focal point of the excitation beam. The molecules comprising the medium at said points of excitation undergo a chemical transformation that renders them fluorescent upon irradiation with visible light. Information stored in the aforementioned manner can be subsequently retrieved or "read" with three-dimensional resolution by monitoring the fluorescent emission of the "written" micro-domains.

The optical storage materials and the storage/retrieval methods of the present invention are capable of storing data at densities of up to 1 gigabyte/$cm^2$. The reading and writing processes for storage and retrieval of data onto and from the optical media of the invention is readily accomplished by the read/write apparatus of the invention which comprises a laser source, a focusing lens assembly, scanner and an avalanche photodiode detector (ADP). The light source from the laser is focussed at predetermined specific locations within the optical media material. The energy of the light source is controllable and can be set at optimal values to perform either a write or a read function. The depth of the focus within the material can be controlled by the lens assembly and allows data to be stored into and retrieved from different depth within the media in a three-dimensional mode. During a read cycle, the fluorescent emission signals emanating from the written domains within the media pass through the same lens assembly, following which they focused onto the active area of the avalanche photodiode detector. Galvanometric scanners can be used for line- or raster-scanning the laser beam at a fast rate to accomplish rapid write and read cycles.

In one aspect, the present invention provides optical storage media capable of having an increased storage density per unit of volume comprising materials that are capable of undergoing energetically differentiated optical processes for initiation of writing and reading modes. The optical recording media comprising the materials of the present invention are writable, readable, and highly durable, that is, they are capable of withstanding a large number of read cycles without loss or elimination of stored data.

In another aspect, the present invention to provides an apparatus for writing to and reading from three-dimensional optical media that are capable of providing differentiated photoactivation energies to initiate said writing and reading processes.

In accordance with the foregoing aspects the optical storage media of the present invention includes an optical storage material capable of storing data in a 3D matrix, and an apparatus for writing to and reading from the storage media. The storage media can be configured to have a finite thickness that inherently includes a plurality of molecular layers, thereby enabling optical storage and retrieval of information or data in a 3-D mode.

BRIEF DESCRIPTION OF THE DRAWINGS

The attributes and features of the present invention are better understood with reference to the following detailed description and accompanying drawings.

FIG. 3 shows fluorescent data written into the optical storage material at different intensities. (a) Two rows of data read at high intensity immediately after writing. Each row shows the same intensity and background level upon readout. (b) Same data read at low intensity after the upper row of data has been read consecutively 500,000 times shows that photobleaching due to multiple read cycles is minimal, and the data can still be distinguished readily from the background.

DETAILED DESCRIPTION OF THE INVENTION

Figure 1:
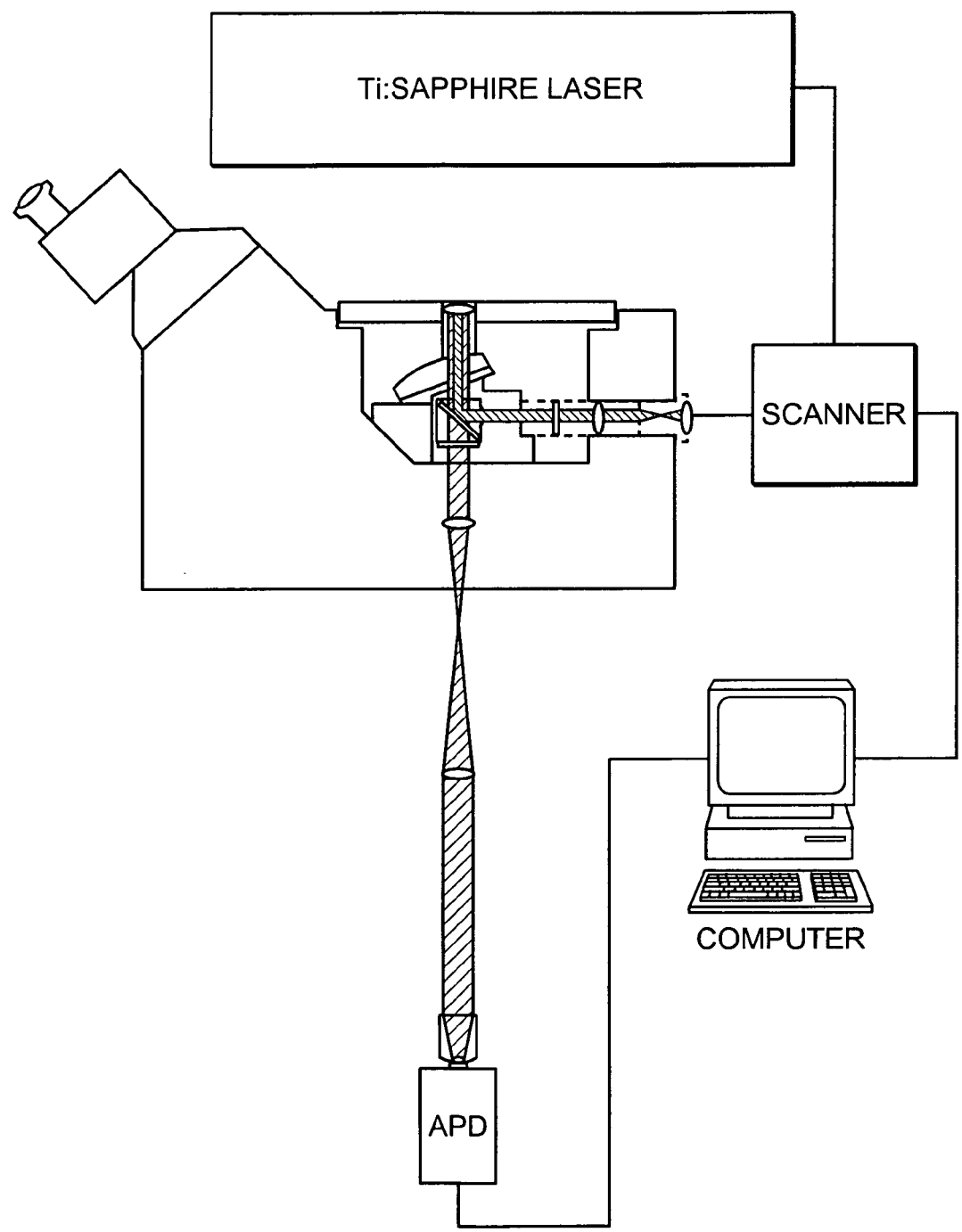
FIG. 1 shows a schematic setup for the writing into and retrieval from the optical storage material of the invention.

The present invention relates to optical storage materials for producing high memory capacity optical storage media, and methods for information storage (writing) and retrieval (reading) from said storage materials comprising the said storage media in a three-dimensional, multi-layered format. The present invention also provides apparatus and methods to accomplish three-dimensional optical writing and reading from said optical storage media. More particularly, the present invention provides a class of optical storage materials comprising polyaromatic compounds, particularly bisphenol, phthalein diethers and their substituted derivatives, for optical data storage.

The compounds of the invention when heated either to or above their melting points and subsequently cooled to ambient temperatures form "molecular glasses" that possess a memory attribute that confers in them the ability to store and retain optically encoded information. In their glassy state, the said compounds fluoresce strongly when subjected to a multi-photon excitation (MPE) process by a laser source. Data storage using optical media of the invention that comprise said compounds is accomplished by the writing method of the invention. The said method utilizes location specific photo-irradiation to initiate an MPE process that causes chemical transformation of molecules located in the irradiated micro-domains within the molecular glass to be transformed into fluorescing moieties. The written or stored information can be subsequently retrieved by optically reading the created photoactivation pattern. Since fluorescing molecules are generated only in specific micro-domains within the media where the excitation beam is incident, and only proximal to the focal point of the laser beam, writing and reading of information in a three-dimensional format is enabled by focusing the incident beam at varying depths within the optical media. The power and the duration over which the writing beam is incident on the media can be varied to produce written bits of different volumes. Writing densities of up to 1 gigabyte per square centimeter can be achieved using the materials and methods of the invention. Reading of stored information can be accomplished by the method of the invention wherein a photoexcitation "reading" beam causes molecules in the written domains to undergo a multi-photon absorbance, and the resulting fluorescence emitted from said domains is optically detected by the detection apparatus of the invention. The reading beam can be optimized to maximize the signal-to-noise ratio (S/N) of the written bits, thereby increasing sensitivity, while substantially minimizing memory degradation from multiple reading cycles.

Another aspect of the optical media of the invention that is a key feature to their durability, that is, ability to withstand multiple read cycles (up to 2,000,000 reads) of written material without suffering memory degradation due to overwriting or photobleaching is that the multiphoton processes for the write and read modes are substantially different in terms of energy requirements. The write process is a three-photon process and requires energies that are substantially greater than those used for the read cycle, which is a two photon process with a lower energy requirement. The reading process therefore, does not cause inadvertent overwriting that can result in memory degradation.

Information is written in the media as a result of an MPE step initiated within the volume comprising the by a highly focused mode-locked laser, that causes an MPA process within the media at the focal point of the excitation beam.

Multi-photon excitation/absorbance (MPE/MPA) refers to the simultaneous excitation by and absorption of two (or more) photons by a chromophore molecule. In multi-photon excitation process, an intense light source is employed, since a single photon of the light from this source is not sufficiently energetic to cause absorption by chromophore molecules, but two or more photons have sufficient energy. If the requisite number of photons is present simultaneously, an MPA event can occur. The probability of an MPA event occurring is proportional to the light intensity or power of the source (number of photons per unit area) to the power of the requisite number of photons. MPA is therefore more efficient when short-pulsed lasers with high peak intensities are utilized.

The essential characteristic of the MPA process is that the plurality of photons must simultaneously impinge on the molecule. The excitation rate, therefore, is proportional to the incident intensity to the power of the number of photons that must be absorbed. Excitation is thereby mainly confined to the ellipsoidal focal volume where the intensity is extremely high. Such excitation is produced, in the preferred form of the invention, by a laser source that provides sufficient incident intensity to produce simultaneous absorption of two or more photons by the molecules comprising the glassy optical storage materials, each photon having one over the number of photons required of the energy respectively required for normal single photon absorption.

A two-photon absorption is the simultaneous absorption of two photons of light, neither one of which is sufficient on its own to cause the molecule in question to changes its electronic state. A three-photon absorption is the simultaneous absorption of three photons of light, no pair of which is sufficient on its own to cause chromophoric molecules to change their electronic state. The photons may be of the same wavelength, or a combination of different wavelengths.

The molecules comprising the medium at said points of excitation undergo a chemical and/or physical transformation that renders them fluorescent upon irradiation with visible light. Information stored in the aforementioned manner can be subsequently retrieved or "read" with three-dimensional resolution by monitoring the fluorescent emission of the "written" micro-domains The optical storage materials that are used to fabricate the optical storage media are a class of low-molecular-weight compounds that, when exposed to temperatures at or above their melting point, followed by subsequent cooling of the molten state, form optically clear (transparent glasses) that are stable at or below ambient temperatures. Compounds that exhibit this characteristic i.e. formation of a glassy state (herein referred to as molecular glass) include polyaromatic compounds containing two or more phenyl groups, such as for example, biphenyl, diphenylmethane and substituted derivatives thereof. In a preferred embodiment, the molecular glass forming materials are phthalein compounds such as for example, compounds derived from phthalic anhydride, and most preferrably, phthalein diethers including phenophthalein diethers and their substituted derivatives. The general classes of molecular glass forming compounds of the invention, as shown by formulas I–IV.

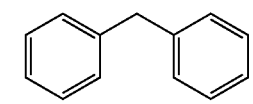

I

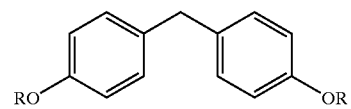

II

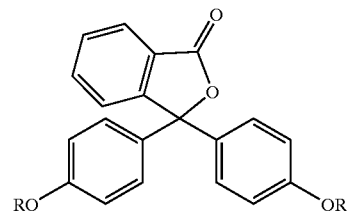

III

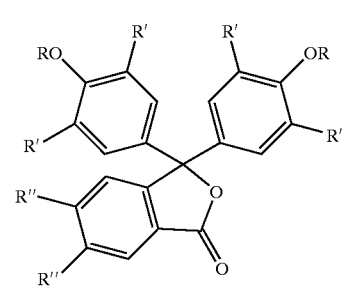

IV wherein R, R' and R" each independently comprises H, halogen atom or halogen-containing moiety, alkyl, alkenyl, alkynyl, aryl, alkoxy, alkenyloxy, alkynyloxy, aryloxy, alkoxy carbonyl, alkylamino, alkylthio, alkylsulfonyl and alkylsulfinyl, each optionally substituted with an alkyl, halogen, alkoxy, aryl or heteroaryl moietys.

In a preferred embodiment, the preferred phthalyldiether compounds of the invention are phenolphthalein dimethyl ether V and ortho-cresolphthalein diether VI.

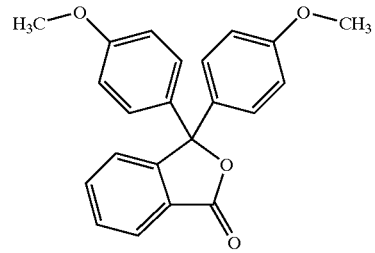

V

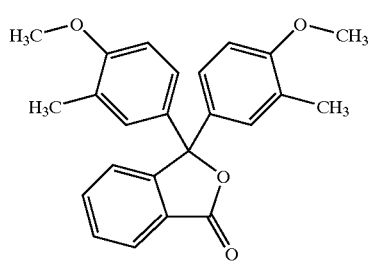

VI

Ortho-cresolphthalein dimethylether VI is prepared in high yield in a single-step from the o-cresolphthalein, and forms a glass near room temperature, with a $T_g$ of 310° K. In one embodiment, samples for recording and storing data are prepared by melting about 15 mg of VI ($T_m$=387° K.) on a clean glass coverslip, and allowing it to cool to room temperature to form a transparent, colorless glass that is resistant to crystallization.

Chemical synthesis of the preferred phthalyldiether compounds of the invention can be accomplished by the reacting phthalic anhydride or substituted derivatives thereof with either phenols or substituted phenols (Scheme 1), or with anisole or their substituted derivatives (Scheme 2) as shown below.

Scheme 1

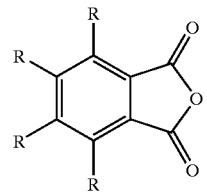
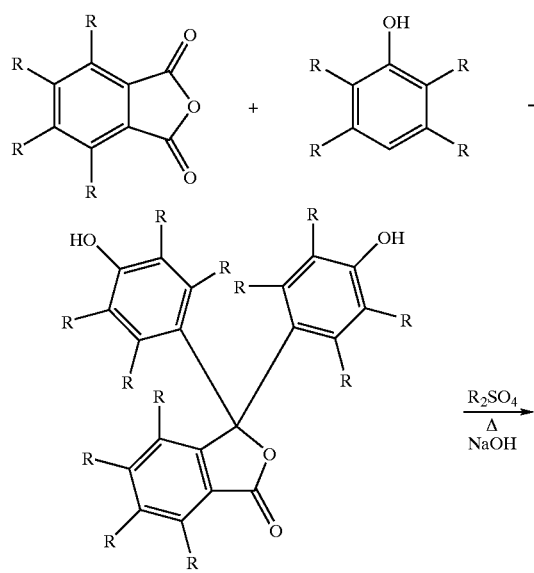

-continued

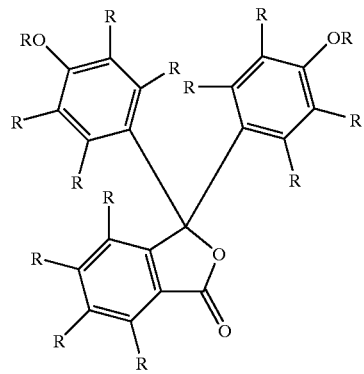

R = H, halogen, alkyl, alkenyl, alkynyl, aryl, alkoxy, alkenyloxy, alkynyloxy, aryloxy, alkoxy carbonyl, alkylamino, alkylthio, alkylsulfonyl, alkylsulfinyl Scheme 2

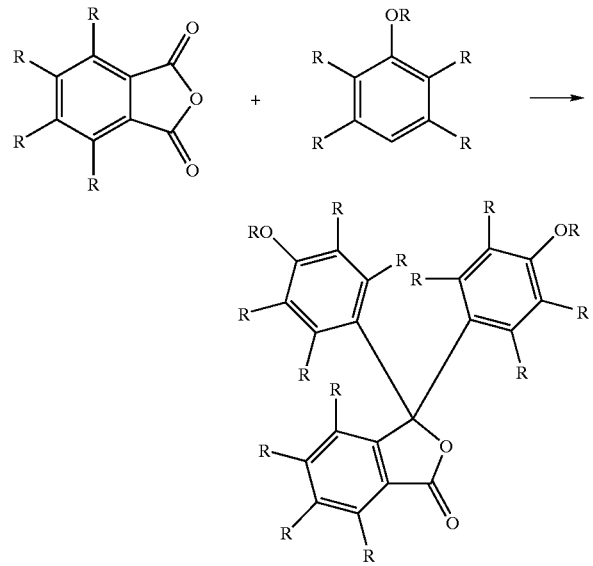

R = H, halogen, alkyl, alkenyl, alkynyl, aryl, alkoxy, alkenyloxy, alkynyloxy, aryloxy, alkoxy carbonyl, alkylamino, alkylthio, alkylsulfonyl, alkylsulfinyl In a preferred embodiment, the molecular glass-forming compounds shown by the general formula IV are diethers of phenolpthalein and substituted derivatives thereof. They can be obtained by a general preparative reaction shown in Scheme 1, wherein a phthalic anhydride compound VII is condensed with a molar excess of a phenolic compound VIII to form the corresponding 1:2 adduct IX. Etherification of the phenolic groups in IX is accomplished by reacting it either with a sulfate of the type $R_2SO_4$ in the presence of a strong base such as sodium hydroxide (NaOH) in water or, alternatively, with a halide, such as for example, an alkyl iodide of the type RI, in the presence of a weak base such as potassium carbonate ($K_2CO_3$) in dimethyl sulfoxide (DMSO) to give the corresponding phthalyl diether compound X. Alternatively, phthalic anhydride compound VII is condensed with an anisole compound XI under controlled reaction conditions as shown in Scheme 2, whereby the corresponding phenolpthalein diether XII is obtained directly, and eliminating the etherification step.

The compounds comprising the optical storage materials of the invention are excellent glass forming compounds. High-quality glasses can be formed by heating the materials above their melting points and allowing the molten materials to cool to ambient temperature. In one embodiment, the molten materials of the invention are allowed to cool to ambient temperature in a mold, which defines the predetermined final shape for the resulting glass. High quality as described herein means primarily to high optical quality for the glassy form of the materials that are transparent, colorless and non-fluorescent; they do not exhibit fluorescence until being subjected to an MPA process. The resultant glassy materials of the present invention are optically transparent, resistant to crystallization and cracking, and can be processed (e.g., polished) as needed. Furthermore, they are insusceptible to deformation or discoloration even upon aging over extended periods (several years).

In another embodiment, the optical storage materials of the invention may be incorporated in an independently glass-forming material with a $T_g$ that is at or above room temperature wherein said storage materials are soluble. Examples of such independently glass-forming materials include sugar/water glasses such as for example, trehalose, ionic glasses such as LiCl/water, high molecular weight (HMW) molecular glasses such as sucrose benzoate and polymeric glasses such as polyvinyl chloride (PVC), polymethylmethacrylate (PMMA), polystyrene (PS) and polycarbonate (PC).

In a preferred embodiment, a homogeneous mixture of the storage material and independently glass-forming material is prepared by either by I) heating a mixture containing both materials on a suitable substrate to an elevated temperature above their individual melting points, and subsequently forming a glass by cooling the molten mixture or ii) by dissolving both components in a suitable solvent or solvent mixture, coating a substrate with the resulting solution, followed by rapid removal of the solvent(s) by standard methods, such as those utilized in spin coating in solution, to provide a high quality glassy layer or film as a coating on the substrate surface.

In another embodiment, the photoactivatiable the optical storage material molecules (OSMM's) may be bonded to a polymeric host matrix either as an ionic complex, or through covalent chemical bonds. Covalent attachment to a polymeric matrix can be accomplished, for example, by introducing one or more substituents containing a polymerizable functionality. In a preferred embodiment, the phthalein compounds of the invention are mono or di-functionalized with an acrylate or a methacrylate moiety, for example, by reacting phenolphthalein with acryloyl or methacryl chloride. The functionalized molecules function as monomers that may be pollymerized by thermal or photochemical methods. In another embodiment of the invention the phthalein compound is functionalized with an acrylate or methacrylate moiety comprising an alkyl or alkyloxy spacer such as a hydrocarbon or a polyethylene glycol (PEG) chain. In yet another embodiment, phthalein compounds may be reacted directly with to form an epoxide resin.

In another embodiment molecules comprising the optical storage materials of the invention may be directly immobilized on a substrate surface via a either ionic or covalent linking. The said compounds are functionalized with substituents that are capable of providing ionic or covalent linkage with the substrate surface. Alternatively, the substrate surface is derivatized with the linker moiety, following which OSMM's are immobilized to the derivatized surface via either ionic or covalent chemical bonding. In a preferred embodiment, a glass substrate is functionalized with either a triethoxy or trichlorosilane that contains an acrylate or a methacrylate substituent, following which the OSMM's are subsequently coupled to form the corresponding acrylate or methacrylate ether derivative as described previously.

In another embodiment, the photoactivatable OSMM of the present invention can be doped in another medium such as a porous medium (e.g., sol-gel glass). In a preferred embodiment, the dopant OSSM concentration is ranges from about 0.1% to about 50% by weight. In yet another embodiment, a layered structure comprising a plurality of layers of the photoactivatable OSSM of the invention in an alternating arrangement with a spacer layer possessing desired optical or electrical properties.

The glassy molecular data storage materials comprised in the optical storage media of the present invention can also be glassy polymeric materials containing photoactivatable aromatic moieties having a glass transition temperature ($T_g$) that is at or close to ambient temperature. Glassy polymeric materials of the present invention that are capable of functioning as data storage materials include, and are not limited to aryl epoxy polymers, aromatic poly amines and amine-epoxide polymers containing photoactivatable aromatic moieties.

In one embodiment, the glassy polymeric data storage material is a polymer derived from a bisphenol diether monomer (resin) having a general formula XIII wherein the bis-phenolic group functions as the photoactivatable moiety.

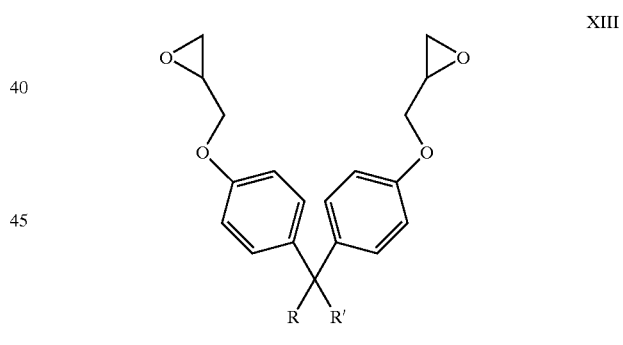

XIII

The epoxy resin for synthesis of the glassy polymeric optical storage materials of the present invention can be either a glycidyl epoxy including glycidyl-ether, glycidyl-ester and glycidyl-amine epoxy resins, or non-glycidyl epoxy resins such as aliphatic or cycloaliphatic epoxy resins. Glycidyl epoxy resins useful for optical data storage are prepared via a condensation reaction of appropriate dihydroxy compound, dibasic acid or a diamine and epichlorohydrin, while non-glycidyl epoxies are formed by peroxidation of olefinic double bond.

In one embodiment, the glycidyl-ether epoxies used for the synthesis of glassy polymeric optical storage materials of the invention is a commercially available diglycidyl ether of bisphenol-A (DGEBA) or a novolac epoxy resin, the structures of which are shown below.

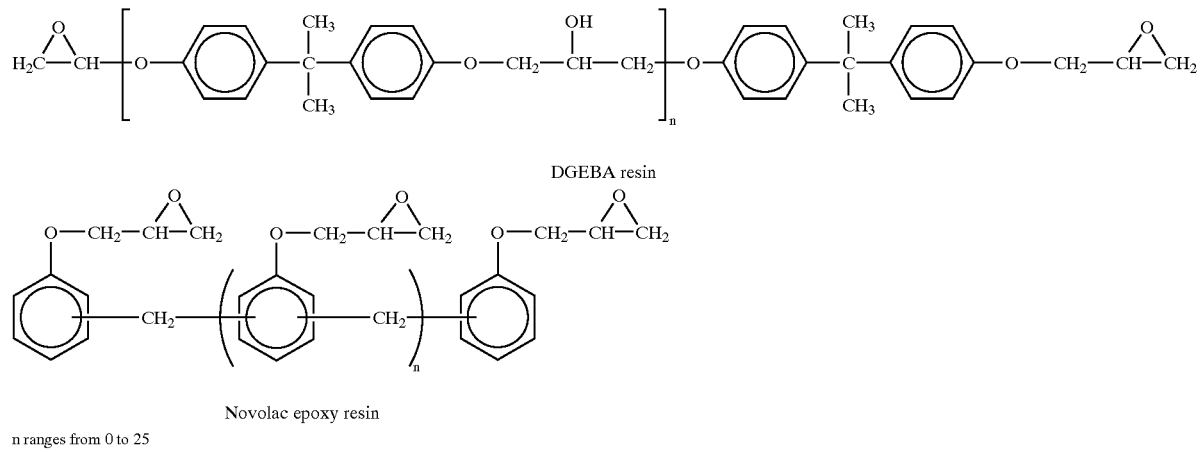

DGEBA resin

Novolac epoxy resin n ranges from 0 to 25

In a preferred embodiment, the polymeric glassy material is an optically clear epoxy polymer which is obtained by curing DGEBA with a hardener at ambient temperature using standard conditions known in the art, since it is a major constituent of the resin in many epoxy formulations.

Curing agents or "hardeners" utilized for obtaining the polymeric glassy materials of the present invention from glycidyl ether resins such as DGEBA include, but are not limited to amine based curing agents that comprise primary and secondary amines, such as for example, 4,4'-methylenebis-[chloro-2,6-diethylaniline] (MCDEA), 4,4'-diaminodiphenylsulphone (DDS), 4,4'-dimethylaniline (MDA) and tris(dimethylaminomethyl)-phenol, cationic curing agents such as N-benzylpyrazinium-10-hexafluoroantimonate (BPH), N-benzylquinoxaliumhexafluoroantimonate (BQH) and anhydrides such as alkenyl succinic anhydrides including 2-octenyl, 2-dodecynyl and 2-hexadecenyl succinic anhydrides. Phenol based hardeners are preferred for curing phenolic novalac epoxy resins. Optionally, a catalyst, commonly known as an "accelerator" can be used to induce a faster rate of cure. Typical accelerators include tertiary amines and triphenylphosphine.

In a preferred embodiment, the resin for obtaining the glassy polymeric data storage material of the present invention is Devcon 5-Minute Epoxy™ comprising DGEBPA resin and a polymercaptan/polyamine hardener mixture composed of tris(dimethylaminomethyl)-phenol and a polymercaptan curing agent.

The optical storage molecular glass forming material of the invention can be converted to the corresponding optical storage media by pre-forming a glassy film of the material on a suitable substrate. In a specific example of a preferred embodiment, the crystalline glass forming material is heated on a glass substrate to its melting point, and the resulting liquid is cooled to form an optically transparent glass, which is subsequently sandwiched between two layers of glass. The resulting configuration is used as a storage media for optically recording or writing information.

Optical data storage in the storage media of the invention can be accomplished by using an optical source, for example, a laser source beam to initiate an MPA process in the molecular glass material within the storage media to "write" information whereby molecules in the written areas or micro-domains are transformed into species capable of emitting fluorescence. MPA causes the materials undergo an irreversible photochemical transformation that renders the region in the focal volume of the laser fluorescent. Writing of data in this manner can be accomplished with pulse energies that are typically in the range of 0.25 nJ with dwell times in the millisecond range, while readout can be accomplished at one tenth of this pulse energy.

The reading and writing processes for storage and retrieval of data within and from the optical media of the invention is readily accomplished by the read/write apparatus of the invention which comprises a laser source, a focusing lens assembly, scanner and a detector, such as an avalanche photodiode detector (ADP). The light source from the laser is focussed at predetermined specific locations within the optical media material. The energy of the light source is controllable and can be set at optimal values to perform either a write or a read function. The depth of the focus within the material can be controlled by the lens assembly and allows data to be stored into and retrieved from different depth within the media in a three-dimensional mode. During a read cycle, the fluorescent emission signals emanating from the written domains within the media passe through the same lens assembly following which they focused onto the active area of the avalanche photodiode detector. Galvanometric scanners can be used for line- or raster-scanning the laser beam at a fast rate to accomplish rapid write and read cycles.

A typical set up for a write-read apparatus in a preferred embodiment is shown in FIG. 1, which comprises a Ti:sapphire laser connected to a computer, scanner and avalanche photodiode detector (ADP). The Ti-sapphire laser produces approximately 70-fs pulses with a center wavelength of about 800 nm at a repetition rate of about 76 MHz. The laser is reflected off of two galvanometric scanning mirrors into the rear port of an inverted microscope. The laser beam is reflected off of a dichroic mirror into an infinity-corrected objective that focuses the light into the sample. Fluorescence from the sample passes through the same objective and then through the dichroic mirror before being focused onto the active area of a low-noise avalanche photodiode detector. The galvanometric scanners can be used for line- or raster-scanning the laser beam at a fast rate, while the microscope stage can be controlled separately with 0.1 μm resolution. The depth of focus of the laser beam within the storage material is controlled by moving the objective itself.

In another embodiment, the objective lens assembly can remain fixed while the storage of recording media is moved in a controlled manner relative to the objective lens to vary the depth of focus within the media.

Figures 2A, 2B, 2C:
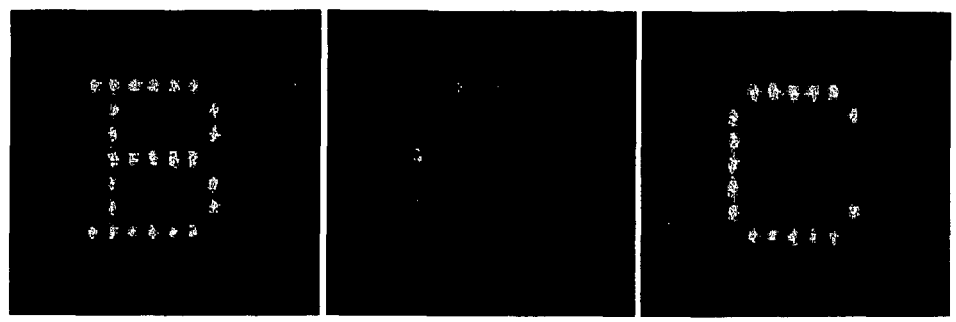
FIGS. 2A, 2B and 2C show images of representative fluorescent data stored in three planes of a thin sample of compound V. The interplane separation is 1250 nm, and virtually no crosstalk is apparent in planes that are separated by 2500 nm.
Figure 2D:
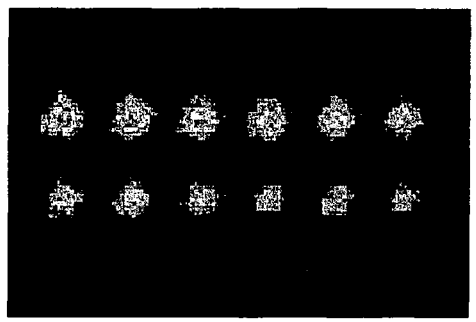
FIG. 2D shows the image of two rows of fluorescent data, each representing the bit pattern 10101010101. The lower row has been read 1.5 million times.
Figure 2E:
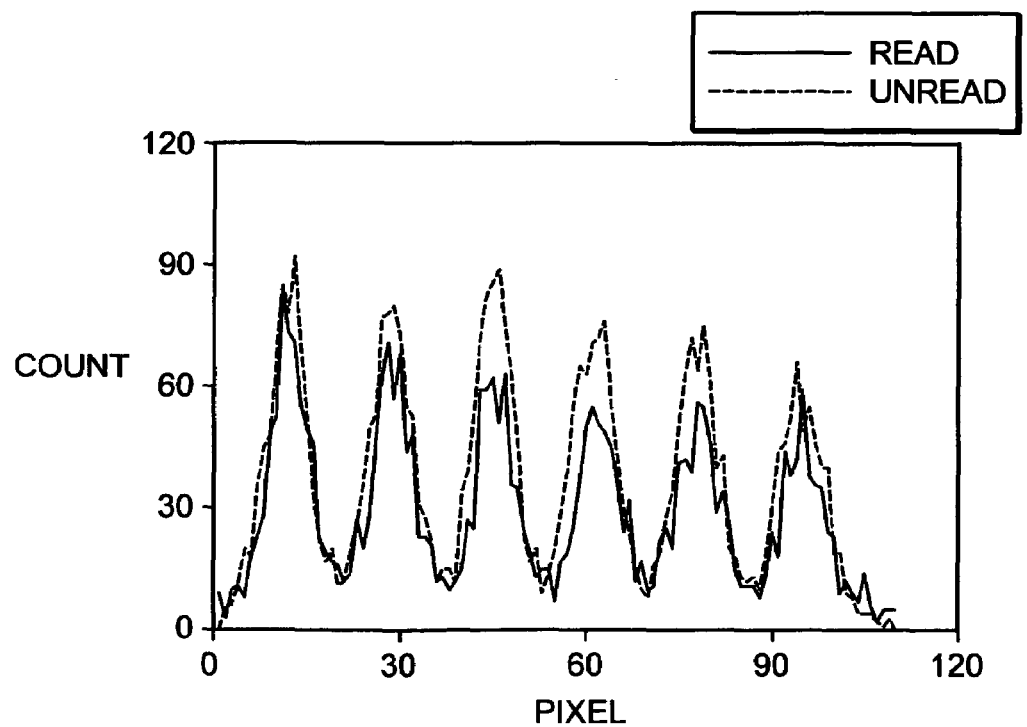
FIG. 2E shows the intensity pattern along the central pixel of each row of data in FIG. 2D.

The optical storage media of the present invention provides high storage densities (capacity) that are determinable by fluorescence methods. In a preferred embodiment, the 3-D storage density of V is determined by writing fluorescent spots at different positions in the sample for about 8 seconds at an average power of about 2.3 mW (power is that measured at the sample) Images are then read out at an average power of about 0.7 mW with a scan time of about 35 ms/line. FIGS. 2A, 2B and 2C show typical readout images of three planes in the sample, the first and third of which have had fluorescent data stored in them. The separation between in-plane bits in these images is about 600 nm, and the planes in the successive images are separated by about 1250 nm. As seen from FIGS. 2A and 2C, an interplane separation of about 2500 nm is sufficient to suppress cross-talk. Up to 25 planes of data can be written with such interplane separation, which corresponds to a storage density of approximately 870 megabytes per square centimeter of a thin sample (about two orders of magnitude larger than the storage density of a standard compact disk). The storage density in the optical media of the present invention can be improved substantially (several-fold) by utilizing an objective that is optimized for the index of refraction of compound V (approximately 1.61), and by storing data on both faces of the sample. Also, data storage and readout can be accomplished far more rapidly at higher intensities, which are readily available from a Ti:sapphire oscillator. The robustness of stored data to readout is tested by writing two parallel rows of data with the pattern 10101010101, where 1 is represented by a fluorescent spot and 0 by a dark spot. The lower row of data is then read repeatedly at an average power of about 0.7 milliwatts (mW), and both rows are imaged periodically at this same power. FIG. 2D shows an image of the two rows of data after the lower row has been read 1.5 million times. As shown in cuts through the center of each row of data in FIG. 2E, there is no difficulty in discerning zeroes from ones after multiple readout cycles. Readout causes minimal photobleaching of the bright bits, and virtually no photoactivation in the dark bits.

The extreme robustness of data written into the optical storage media of the invention are to the "read" process is further exemplified in FIG. 3. The upper panels of FIG. 3 show two rows of data written with increasing source intensities ranging from 5 to 10 mW (from left to right); the lower panels show the corresponding measured fluorescence intensity as a function of position through the center of each row. Comparison of the same written data read at high intensity (5–10 mW) immediately after writing (FIG. 3a) and at low intensity (1–2 mW) (FIG. 3b) wherein the upper row of data is shown after being read 500,000 times (equivalent to retrieval or "playing back" of a conventional 2-D compact storage disk 500,000 times, or about 57 years of continuous "read" time) indicates that written data can be readily discerned from the background, and is substantially unaffected after multiple read cycles. Also, stored data is accurately readable several months after the "write" process. Information written into the storage media of the invention is extremely stable compared to conventional media using comparable source intensities, since they are susceptible to degradation due to either photobleaching or overwriting.

Figure 4A:
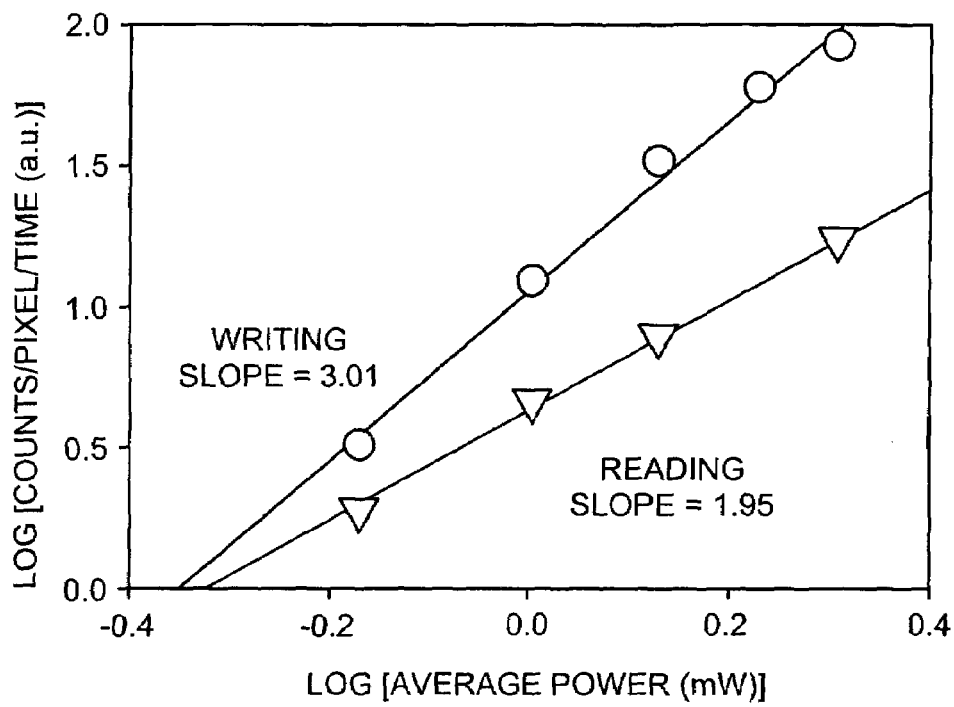
FIG. 4 shows (A) Log-log plots of counts/pixel/time versus average laser power for a three-photon process data storage (writing) and a two-photon reading process using 800-nm source; and (B) Readout counts as a function of temperature for data stored at an average power of 1.7 mW for 5.5 seconds and read at an average power of 0.7 mW (dashed line denotes $T_g$).

The high stability (robustness) of stored data in the storage media of the invention is attributed to the differential energy requirements for initiation of the MPA processes for the write and read cycles respectively. The intensity dependence of the data storage process is determined by writing spots for a fixed amount of time at different average laser powers and then reading the data at a fixed power. The number of photons involved in the write and read processes can be determined from the slope of a log-log plot of the intensity data as a function of the average power at the excitation wavelength. As seen in FIG. 4A, a logarithimic plot of the fluorescence intensity of stored data as a function of the writing intensity of the source excitation beam (at about 800 nm) is linear with a slope of about 3. Since the fluorescence intensity shows an exponential dependence on the writing intensity, the exponent of writing intensity is determinable from the slope of such a plot, which indicates that data storage in the optical media of the present invention is a three-photon process. A similar plot for the readout process is also linear with a slope of approximately 2, indicating that readout is a two-photon process at the 800-nm excitation region. Thus, because data storage is a 3-photon process, it requires relatively higher intensity than does the 2-photon readout process. The data retrieval or "read" process can therefore, be accomplished substantially free of parasitic overwriting and memory degradation. Thus, although data storage is an efficient three-photon process at 800 nm, readout can be accomplished at considerably lower intensities, thereby avoiding photoactivation of the dark areas of the sample that are scanned.

Figure 4B:
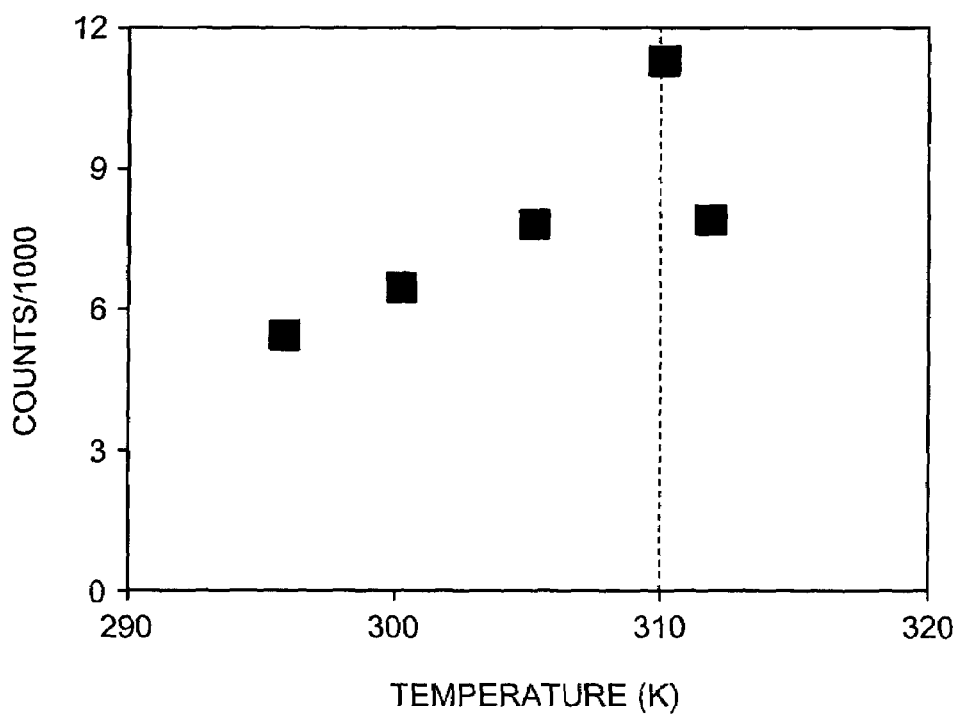
Figure 5B:
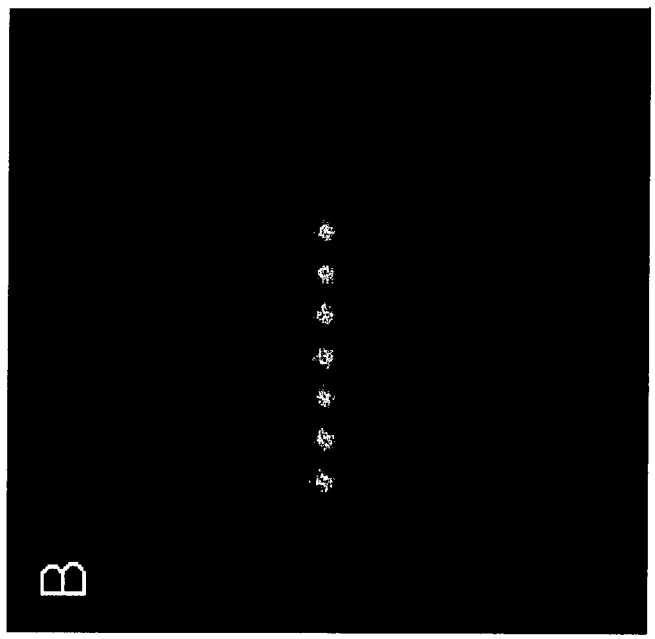
FIG. 5 shows fluorescent images after a write cycle in the glassy polymeric optical storage material derived 5-Minute Epoxy™. Fluorescent spots cannot be written into freshly-mixed hardener and resin using intensities in the range used to store data in low molecular weight glassy material V (FIG. 5A), but can be written readily in the resin/hardener mixture once it has aged for five minutes or longer (FIG. 5B).
FIG. 5C shows an image of two rows of data, each with a data pattern of 10101010101 (lower row after two million read cycles).
FIG. 5D shows the intensity pattern through the centers of the two rows. There is insignificant photobleaching in stored (bright) areas after read cycles and no significant photoactivation of dark (blank) regions.
Figure 5C:
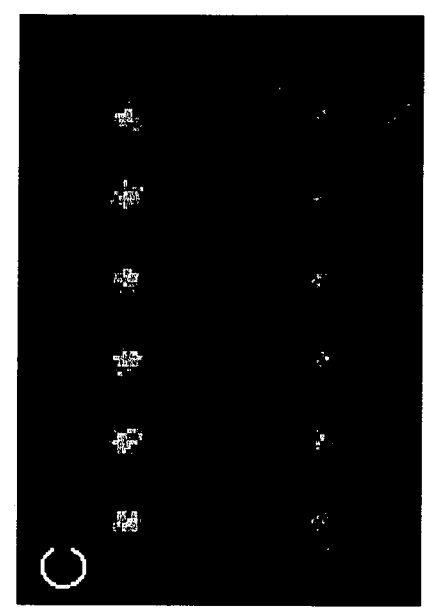
Figure 5A:
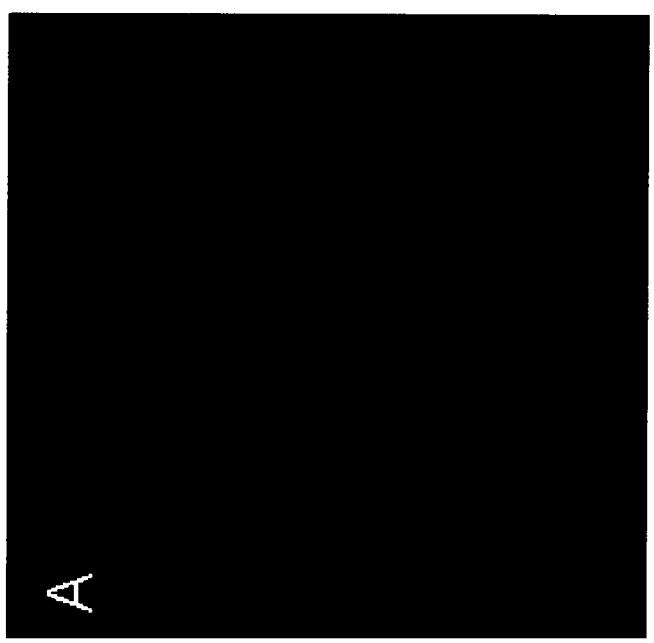
Figure 5D:
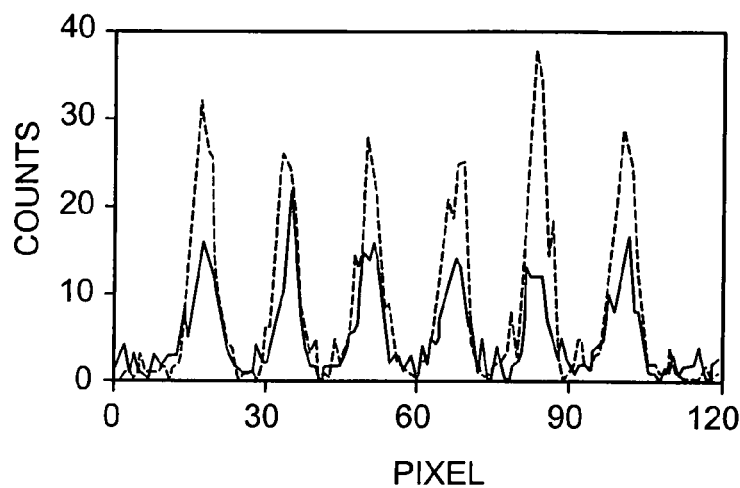

The glassy nature of the storage media of the present invention plays an important role in the robustness of stored data to readout. Readout intensity of spots that are written and read under identical conditions at different temperatures on compound V (FIG. 4B) demonstrate that data storage is more easily accomplished near $T_g$, and that the storage efficiency decreases both above and below $T_g$. This tendency is indicative that a certain degree of molecular flexibility is pre-requisite for efficient creation of the fluorescent photoproduct, but that the considerably greater configurational freedom available in the supercooled liquid is deleterious to the formation of this product. A similar study performed on optical media obtained from glassy phenolphthalein dimethyl ether (VI) indicates that the data storage efficiency continues to decrease as the temperature is increased further above $T_g$.

FIG. 5 shows the optical data storage property of a crosslinked polymeric glass data storage material of the present invention when used an optical data storage medium. Fluorescence is not induced in either the pure resin or the hardener prior to mixing after exposure to light intensities comparable to those used for data storage in low molecular weight glass V. While photoactivation in this intensity range is also not possible immediately after mixing of the hardener and resin (FIG. 5A), photoactivation becomes viable at these intensities when the polymerization or curing process begins (low cross-link density), with an efficiency that increases with time until the mixture hardens completely (moderate crosslink density) (FIG. 5B). The writing process becomes significantly less efficient when resin-hardener mixtures are cured at elevated temperature (high cross-link density, implying that restricted conformational mobility greatly improves the efficiency of photoactivation. Optical data storage performed on moderately crosslinked polymeric glassy materials of the invention can, therefore, be "locked" within optical recording media comprising such glasses by subsequently curing them at elevated temperature. Accidental overwriting or erasure of stored data can be thus precluded in the "locked" mode. The robustness of data storage in the set (but uncured) epoxy samples although slightly lower than that for low-molecular weight glass V (FIGS. 5C and 5D) is still superior to that of conventionally used materials. No difficulty is encountered in discriminating between light and dark bits, and data degradation due to photobleaching is minimal.

Figure 6:
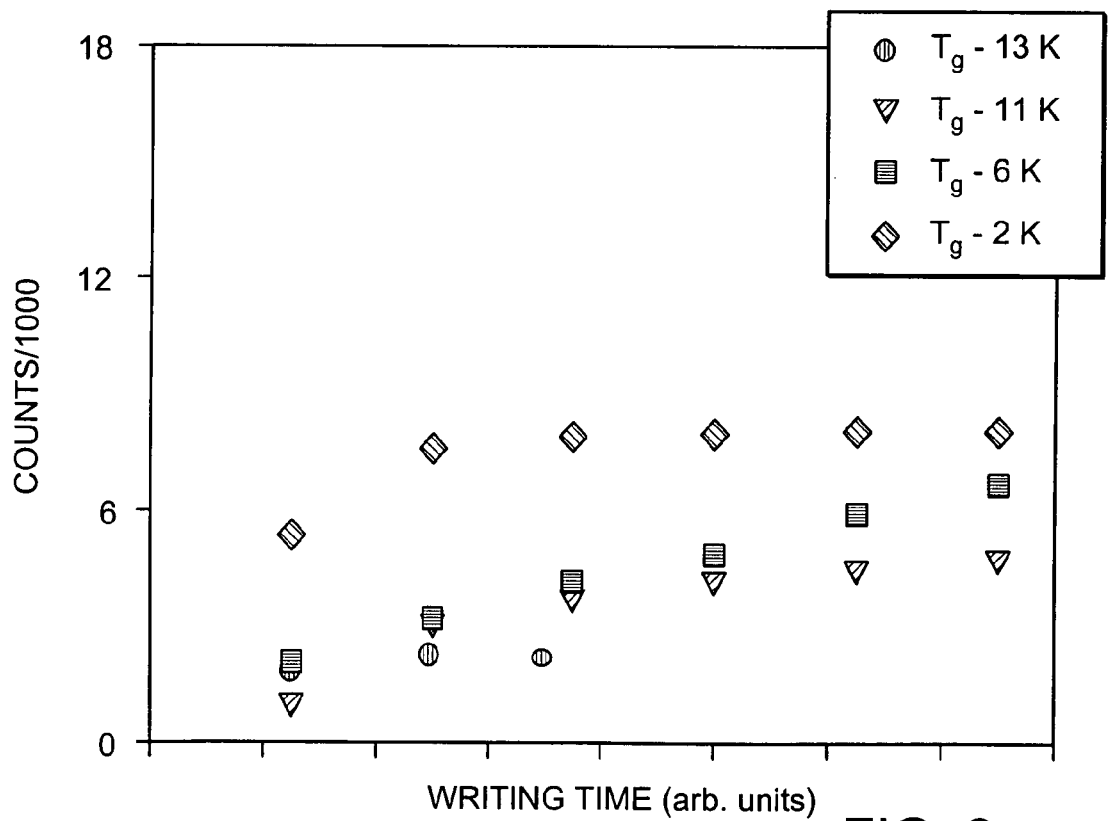
FIG. 6 shows the temperature dependence of the MPA writing process in a glassy material. Data storage is considerably more efficient as the glass transition temperature is approached.

The efficiency of the writing process and stability of written data in the storage media of the invention, therefore, exhibits a temperature dependence that is a key factor in their ability to provide stable long-term data storage without degradation from to time of storage or multiple reads. The writing efficiency into the "molecular glass" storage materials of the invention comprising the storage media increases the as the glass-transition temperature ($T_g$) of the glassy materials is approached. As shown in FIG. 6, the writing process is considerably more efficient near the $T_g$ of the glassy material. As the temperature of the glassy material approaches its $T_g$, the photoactivation process occurs more quickly. Upon cooling, photoactivation becomes significantly more difficult. As is evident from the figure, the fluorescent counts measured from written domains as a function of writing time is greatest when material temperature is maintained close to its glass transition (i.e. $T_g-2°$ K.) for a specific write time, compared to temperatures well below it, for example, at $T_g-13°$ K. Since the glassy state restricts molecules from acquiring adequate degrees of freedom to undergo an MPA mediated photochemical transformation to produce the fluorescent species, and such structural freedom can be achieved in the supercooled liquid state immediately above the material $T_g$, laser-induced heating that can occur locally during the write process thereby facilitating storage. On the other hand, because the thermal conductivity of these materials is large enough that at the intensities at which reading is accomplished, localized heating that can cause the material to exceed $T_g$ is precluded. Therefore overwriting during the read cycles is substantially eliminated. The rigidity of the glassy state also potentially helps in to prevent photobleaching of the fluorescent (written) domains during the read cycles. At room temperature, written information is therefore "locked into place" and is relatively unaffected by the reading beam. Tests on non-optimized, glassy storage materials show that millions of reads are possible with minimal degradation of stored data.

Several aspects of the OSMM's of the invention may be optimized or "tuned" to suit application specific needs. Such optimization includes modification of material properties such as $T_g$, refractive index, chromophore absorption and emission frequencies and processes. Modifiable paramenters and their influence on a specific property or attribute of the said compounds are as follows:

a) Two-photon absorption spectrum and cross section of photoproduct may be modified to optimize readout parameters b) Three-photon absorption spectrum and cross section of the glass may be modified to optimize storage parameters.

c) Fluorescence spectrum and quantum yield of the photoproduct can be modified to optimize readout parameters.

d) $T_g$ may be varied to optimize storage parameters and robustness of stored data e) Substituents providing chemical attachment points may be introduced to tether molecules to a matrix such as a polymeric or porous inorganic medium.

The MPA process used to record and read high-density 3-D fluorescent data in optical storage media of the present invention comprising molecular glasses and glassy polymers provides an added advantage in that it can be performed with an unamplified ultrafast laser system. The stored data is highly substantially more robust to the read process than presently used storage media. Furthermore, glassy materials used in the optical storage media of the invention are relatively inexpensive and obtainable in high optical quality, and can be configured in pre-determined shapes with minimal processing. The glassy materials of the present invention can also can readily modified chemically, thereby allowing their optimization for specific data storage applications. The low laser intensities required by the optical data storage media of the invention for data writing and readout allows for parallelization of both processes so that a multiple spots can be written or read simultaneously.

The optical storage materials of the invention can be utilized in optical storage media configured into a conventional spinning disc format, and therefore, have the potential to produce memory devices that will function in existing formats with an information storage capacity that greater than 100 times that currently available 2-D storage disc media. The optical storage materials of the invention may be also suited for the fabrication of computer generated volume holograms for important applications in optical computing.

There have been described and illustrated herein several embodiments of 3D optical data storage materials, fabrication of data storage media comprising them, and apparatus for storing and accessing information from such media. While particular embodiments of the invention have been described as examples, it is not intended that the invention be limited thereto, as it is intended that the invention be as broad in scope as the art will allow and that the specification be read likewise. Thus, while particular dimensions have been given in examples, it will be understood that the dimensions of the media, including materials and substrates may vary according to available materials and manufacturing techniques. Moreover, while a preferred apparatus set up has been disclosed for the accomplishing write/read processes utilizing storage media of the invention, it will be appreciated that with the benefit of the instant disclosure, other apparati and or configurations for can be used and similar results obtained. In addition, while a single embodiment of laser-optical device has been disclosed, it will be understood that other laser-optical devices can achieve the same or similar function as disclosed herein. In fact, it should be appreciated that different aspects of different embodiments of the invention can be mixed and matched or combined if desired. It will, therefore, be appreciated by those skilled in the art that yet other modifications could be made to the present invention without deviating from its spirit and scope.

Expertimental

EXAMPLE 1

General Synthetic Method for Photoactivitable Pthalein Diethers via Dialkyl Sulfates: Preparation of Phenolphthalein Dimethylethers A 500-mL round bottom flask was charged with 15.0 grams of phenolphthalein and 200 mL of 10% sodium hydroxide solution. 35 mL of dimethylsulfate was added in 5 mL portions while stirring well between added portions. 10 grams of sodium hydroxide was added. The solution was refluxed while stirring for 1–2 hours at 80–90° C. An oil separated from the solution which became a brown solid upon cooling to room temperature. Vacuum filtration was used to collect the solid. The solid was dissolved in warm ethanol and purified by recrystallization. The recrystallized phenolphthalein dimethylether was analyzed by $^1$H NMR. The average yield of this synthesis is ~80%.

EXAMPLE 2

General Synthetic Method for Photoactivatable Phthalein Diethers via Alkyl Halides: Preparation of Phenolphthalein Dimethylether A 500-mL round bottom flask was charged with 5.0 grams of phenolphthalein, 5.0 grams of potassium carbonate, 10–12 mL of iodomethane, and approximately 250 mL of N,N-dimethylformamide (DMF). The solution was refluxed while stirring for 5–6 hours at 70–85° C. Upon cooling, the solution was poured into a 1 L separatory funnel with 100 mL diethylether and 100 mL dilute ammonium chloride. The organic layer from this extraction was added to 150 mL dilute copper sulfate in a separatory funnel. The organic layer was again extracted and 1–2 grams of sodium sulfate was added. This mixture was gravity filtered into a round bottom flask and placed under vacuum to remove the solvent. A highly viscous liquid remained after evaporation of the solvent. This liquid was dissolved in warm ethanol and purified by recrystallization. After recrystallization the phenolphthalein dimethylether was tested for purity via $^1$H NMR. The average yield of this synthesis is ~50%.

EXAMPLE 3

General Synthetic Method for Photoactivatable Bisphenols: Synthesis of Phenolphthalein Phenolphthalein is synthesized by standard methods (insert literature reference here) involving a condensation reaction with phthalic anhydride and phenol under appropriate reaction conditions. Substituted phenolpthalein derivatives are obtained from the correspondingly substituted phthalic anhydride and in a similar manner.

EXAMPLE 4

General Method for Preparation of Cured Epoxy Based Polymeric Optical Data Storage Materials Bisphenol-A diglycidyl ether resin (DGEPBA) was mixed with hardener consisting of a polyamine—polymercaptan mixture (the two part resin-hardener is commercially available under the name Devcon 5-minute epoxy gel resin (ITW Devcon, Danvers, Mass. The resin hardener mixture is applied on the surface of a suitable substrate surface as a film or coating and allowed to harden at ambient temperature. The resulting optical storage medium is used for writing and storing data as described in Example 5. For locking in written data to prevent accidental erasure or overwriting, the storage medium containing the written data is subjected to an elevated temperature cure ranging from 100 to 250° C. over 0.5 to 3 hours to effect higher degrees of cross-links. The data stored in such highly cross-linked media can be read, but are insusceptible to overwriting.

EXAMPLE 5

General Method for Preparation of Optical Storage Media

Approximately 20–25 mg of the glass-forming optical storage materials obtained in Examples 1–3 is placed on a pre-cleaned glass cover slip. The sample is then placed in a 200° C. oven until the crystals have completely melted into a clear liquid. The cover slip is then removed from the oven and allowed to cool to room temperature and allowed to stand for an additional 5–10 minutes.

EXAMPLE 6

General Procedure for Data Storage Utilizing Optical Writing and Reading Methods The optical storage media or the invention prepared according to Example 4 comprising a glass substrate and the storage material is affixed to a glass slide and placed in the sample chamber of a Zeiss Axiovert S100 TV fluorescence inverted microscope, which forms part of the optical data recording apparatus of the invention. The light source is a custom-built, mode-locked Ti:Sapphire oscillator producing sub-100-fs pulses with a center wavelength of 800 nm at a repetition rate of 76 MHz. The oscillator is pumped by a 5-W, diode-pumped, solid-state laser. The beam is directed into the microscope by a set of computer-controlled xy scanning mirrors and is made circularly polarized within the microscope. A dichroic mirror directs the beam into a 40× oil-immersion objective with a numerical aperture of 1.3. An objective heater is used to control the temperature of the material comprising the optical recording medium. Fluorescence emission is collected by the objective and is transmitted through the dichroic mirror into an avalanche-photodiode detection system. The overall collection efficiency of the instrument is 1–2% of the total emitted fluorescence. Writing is accomplished by illumination through a 40× oil-immersion objective with a near-infrared laser beam (Ti:Sapphire, mode-locked ~100 femto-second (fs) pulses, average power 5–10 milliwatts (mW)). Reading from the written storage media is accomplished by scanning an excitation beam over the previously written area. This is performed at a lower power (~1–2 mW), thereby precluding degradation of written data over multiple read cycles. Scanning over the previously written area causes emission of a fluorescence pattern that is detected above background noise, amplified by an avalanche photodiode array (APD) detector and spatially resolved.

The invention claimed is:

1. A method for writing optical data with three-dimensional resolution in an optical storage material comprising a compound of the formula

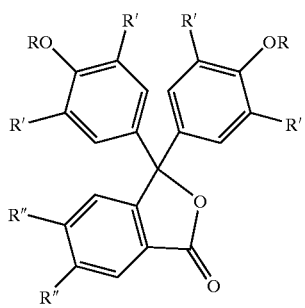

wherein R, R' and R" are each independently H, halogen atom, alkyl, alkenyl, alkynyl, aryl, alkoxy, alkenyloxy, alkynyloxy, aryloxy, alkoxy carbonyl, alkylamino, alkylthio, alkylsulfonyl and alkylsulfinyl each optionally substituted with an alkyl, halogen, alkoxy, aryl or a heteroaryl group comprising the steps of:

a) producing a single intense beam of focusable coherent light; and b) focussing the beam on a photosensitive three-dimensional optical storage medium having the optical storage material to produce at least three photon excitation within said material at the focal point of said beam to thereby produce a detectable characteristic change in said material.

2. The method of claim 1, wherein the characteristic change produced by said at least three-photon excitation is a refractive index inhomogeneity resulting from modification of the density of the optical storage material.

3. The method of claim 2 further comprising scanning said beam through said optical storage material to produce characteristic changes in said material at pre-determined locations to thereby produce three-dimensional inhomogeneities therein.

4. The method of claim 3, wherein the step of scanning said beam includes moving a focal point of said beam in an X-Y plane within said optical storage material to define a plurality of pixel locations in said X-Y plane.

5. The method of claim 4, wherein the step of scanning said beam further includes shifting the focal point of said beam along a Z axis to define a plurality of X-Y planes within said optical storage material, to thereby define a three dimensional array of pixel locations in said material.

6. The method of claim 1 wherein the step of producing a single intense beam of light includes generating from a modelocked laser a stream of coherent light pulses having pulse lengths in the range of 0.1 to 100 fs and having a pulse wavelength of about 600 to 1200 nm.

7. The method of claim 6 wherein the pulse wavelength is 800 nm.

8. The method of claim 1, wherein said compound is

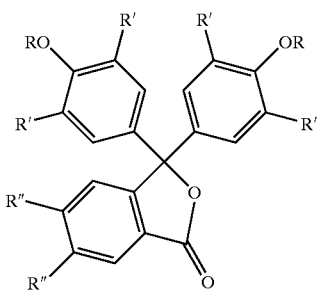

wherein R is each independently alkyl, R' is each independently H and alkyl, and R" is each independently H.

9. The method of claim 1, wherein said compound is

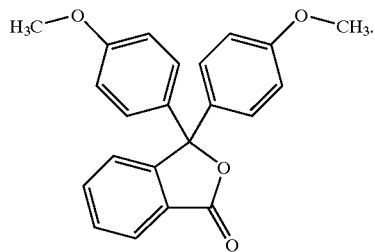

10. The method of claim 1, wherein said compound is

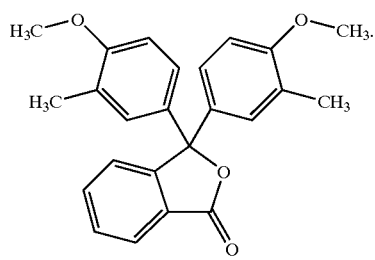

11. The method of claim 1, wherein said compound is a glassy solid.

12. A method of writing and subsequently reading optical data with three-dimensional resolution in an optical storage material comprising a compound of the formula

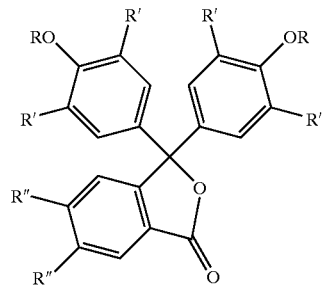

wherein R, R' and R" are each independently H, halogen atom, alkyl, alkenyl, alkynyl, aryl, alkoxy, alkenyloxy, alkynyloxy, aryloxy, alkoxy carbonyl, alkylamino, alkylthio, alkylsulfonyl and alkylsulfinyl each optionally substituted with an alkyl, halogen, alkoxy, aryl or a heteroaryl group comprising the steps of:

a) providing a three-dimensional optical storage medium having the optical storage material that can be modified by the application of light of a predetermined energy;

b) producing a single, intense beam of light and focussing said beam of light at a focal point within said three-dimensional optical storage material;

c) scanning said focal point through said three-dimensional optical storage material to produce at least three photon excitation at pre-determined points in said material to produce a modification of a selected physical or chemical characteristic of the material, each modification representing an optical data bit in said three-dimensional optical storage material; and d) subsequently reading optical data bits produced in said three-dimensional optical storage material by scanning a focused reading beam through said material to produce an interference pattern corresponding to said optical data bits.

13. The method of claim 12 wherein the optical data is stored as a refractive index inhomogeneity in a three-dimensional optical storage material.

14. The method of claim 12 wherein the step of scanning said focal volume includes scanning in X, Y and Z directions through said three-dimensional optical storage material to define a three-dimensional array of data pixels.

15. The method of claim 14 further including directing focused read beams through said three-dimensional optical storage material to produce an image of said three-dimensional array of data pixels to thereby read data stored in said array.

16. The method of claim 12 further including detecting stored data by optically detecting said modification at selected locations.

17. The method of claim 12, wherein said compound is

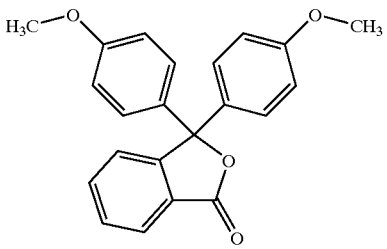

18. The method of claim 12, wherein said compound is

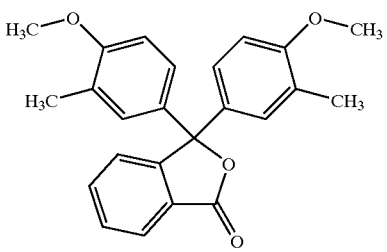

19. The method of claim 12, wherein said compound is a glassy solid.

20. A method of writing and reading optical data with three-dimensional resolution in an optical storage material comprising a compound of the formula

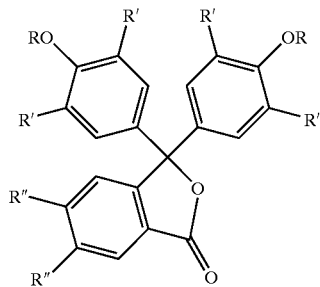

wherein R is each independently alkyl, R' is each independently H and alkyl, and R" is each independently H comprising the steps of:

a) providing a three-dimensional optical storage medium having the optical storage material that can be modified by the application of light of a predetermined energy;

b) producing a single, intense beam of light and focussing said beam of light at a focal point within said three-dimensional optical storage material;

c) scanning said focal point through said three-dimensional optical storage material to produce three-photon excitation at pre-determined points in said material to produce a modification of a selected physical or chemical characteristic of the material, each modification representing an optical data bit in said three-dimensional optical storage material; and d) subsequently reading optical data bits produced in said three-dimensional optical storage material by scanning a focused reading beam through said material to produce an interference pattern corresponding to said optical data bits.

21. The method of claim 20, wherein the compound is

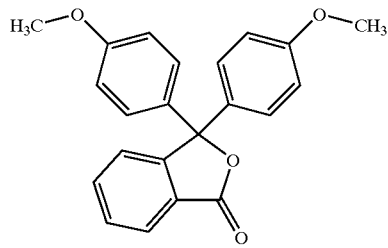

22. The method of claim 20, wherein the compound is

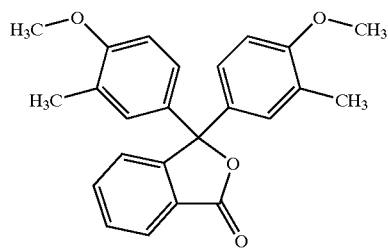

* * * * *